US012392760B2

(12) United States Patent
Huber

(10) Patent No.: US 12,392,760 B2
(45) Date of Patent: Aug. 19, 2025

(54) METHOD FOR MONITORING A CONTAINER TREATMENT INSTALLATION

(71) Applicant: KRONES AG, Neutraubling (DE)

(72) Inventor: Anton Huber, Mainburg (DE)

(73) Assignee: KRONES AG, Neutraubling (DE)

( * ) Notice: Subject to any disclaimer, the term of this patent is extended or adjusted under 35 U.S.C. 154(b) by 277 days.

(21) Appl. No.: 17/982,867

(22) Filed: Nov. 8, 2022

(65) Prior Publication Data

US 2023/0146359 A1 May 11, 2023

(51) Int. Cl.
G01N 33/14 (2006.01)
B67D 7/08 (2010.01)
G01N 1/22 (2006.01)

(52) U.S. Cl.
CPC .............. G01N 33/14 (2013.01); B67D 7/08 (2013.01); G01N 1/2226 (2013.01); G01N 2001/2229 (2013.01)

(58) Field of Classification Search
CPC .............. G01N 33/14; G01N 1/2226; G01N 2001/2229; B67C 3/00; B67C 3/02; B67C 2007/006; B67C 2007/0066; B67C 7/00
See application file for complete search history.

(56) References Cited

U.S. PATENT DOCUMENTS

| 4,932,272 | A | * | 6/1990 | Hogg | G01N 30/20 |
| | | | | | 73/23.35 |
| 6,679,097 | B2 | * | 1/2004 | Kurokawa | G01N 1/2226 |
| | | | | | 73/19.1 |
| 6,874,351 | B2 | | 4/2005 | Bloder et al. | |
| 8,408,043 | B2 | * | 4/2013 | Stehle | G01N 1/2226 |
| | | | | | 73/19.1 |
| 10,156,555 | B2 | * | 12/2018 | Falkenstein | G01N 1/2226 |
| 11,180,356 | B2 | * | 11/2021 | Muszinski | B67C 3/28 |
| 11,726,009 | B2 | | 8/2023 | Germann et al. | |
| 12,181,383 | B2 | | 12/2024 | Lueb et al. | |
| 2013/0275052 | A1 | | 10/2013 | Loder et al. | |

(Continued)

FOREIGN PATENT DOCUMENTS

| CN | 108640068 A | 10/2018 |
| CN | 111733066 A | 10/2020 |
| CN | 111812029 A | 10/2020 |

(Continued)

OTHER PUBLICATIONS

DE-102018216138-A1 merged with machine translation (Year: 2024).*

(Continued)

Primary Examiner — Donnell A Long
(74) Attorney, Agent, or Firm — Caesar Rivise, PC

(57) ABSTRACT

The invention relates to a method for monitoring a container treatment installation which has a filling apparatus for filling containers and a closure apparatus for closing containers. The method involves filling a container with a filling material using the filling apparatus and measuring a concentration of a gas in the filling material of the filled container using a measuring device, wherein the filled container is removed in order to measure the concentration upstream of the closure apparatus or the concentration is measured upstream of the closure apparatus. Advantageously, the method allows the low-oxygen filling by the filling apparatus to be able to be monitored in a selective manner.

20 Claims, 2 Drawing Sheets

(56) References Cited

U.S. PATENT DOCUMENTS

2020/0326264 A1* 10/2020 Germann ............. G01N 1/2226
2022/0048750 A1   2/2022 Winter et al.

FOREIGN PATENT DOCUMENTS

| CN | 112219100 A |   | 1/2021 |   |   |
|----|----|----|----|----|----|
| DE | 10213076 A1 |   | 9/2002 |   |   |
| DE | 102011108133 A1 |   | 1/2013 |   |   |
| DE | 102018216138 A1 | * | 3/2020 | ............. | B67C 3/007 |
| EP | 2629093 A1 |   | 8/2013 |   |   |
| JP | 3383517 B2 | * | 3/2003 | ............. | G01N 23/04 |
| WO | WO2015/036404 A1 |   | 3/2015 |   |   |

OTHER PUBLICATIONS

JP-3383517-B2 merged with machine translation (Year: 2024).*
"Filling System: PFD", Anton Paar GmbH, © 2022, retrieved on Nov. 8, 2022 from https://www.anton-paar.com/de-de/produkte/details/fuellsystem-pfd/.

* cited by examiner

METHOD FOR MONITORING A CONTAINER TREATMENT INSTALLATION

CROSS-REFERENCE TO RELATED APPLICATIONS

This application claims the benefit under 35 U.S.C. § 119(a) of German Patent Application No. DE 10 2021 129 056.2 filed Nov. 9, 2021 entitled METHOD FOR MONITORING A CONTAINER TREATMENT INSTALLATION, and whose entire disclosure is incorporated by reference herein.

TECHNICAL FIELD

The invention relates to a method for monitoring a container treatment installation which has a filling apparatus and a closure apparatus.

TECHNICAL BACKGROUND

Methods and filling apparatuses for filling oxygen-sensitive liquid, such as, for example, beer, in bottles or cans are known per se. For example, oxygen-sensitive products can be filled in a filling process in which the containers are successively evacuated, purged, evacuated, pretensioned, filled and have the pressure reduced. Additional evacuation operations are optionally also possible.

EP 2 629 093 A1 discloses a method and an apparatus for determining the CO2 content in a liquid which is intended to be checked, in particular in a drink.

DE 102 13 076 A1 discloses a method for determining the contained quantities of gases dissolved in a liquid, preferably in a drink, wherein after complete filling of a measurement chamber, which is provided at least with a pressure measurement sensor, with the liquid whose gas content is intended to be checked ("test liquid") and after fluid-tight closure of the measurement chamber, the volume thereof—starting from a standard volume—is increased by a predetermined factor and the equilibrium pressure which has been produced afterwards in the measurement chamber is established and—based on the pressure measurement value obtained in this manner—the gas content of the fluid to be checked is calculated.

A benefit of the invention is to provide an improved monitoring method by means of which it can be established how successful the filling of oxygen-sensitive products has actually been in order where applicable to identify potential for optimisation or sources of error.

SUMMARY OF INVENTION

Benefits are achieved by the features of the independent claim 1. Advantageous developments are set out in the dependent claims and the description.

One aspect of the present disclosure relates to a method for monitoring a container treatment installation which has a filling apparatus (for example, a filling carousel) for filling containers, preferably cans, and a closure apparatus (for example, closure carousel) for closing containers, preferably cans. The closure apparatus is arranged downstream of the filling apparatus (with respect to the container) (for example, connected by means of a transport apparatus between the filling apparatus and the closure apparatus). The method involves filling a container with a (for example, liquid or pasty) filling material using the filling apparatus. The method further involves measuring a concentration of a gas in the filling material of the filled container using a measuring device, wherein the filled container is removed in order to measure the concentration upstream of the closure apparatus or the concentration is measured upstream of the closure apparatus.

Advantageously, the method enables the low-oxygen filling by the filling apparatus to be able to be monitored in a selective manner. The method is particularly suitable for containers which are in the form of cans but can also be used with all other types of containers. Additional disruptive factors or "sources of concern" for the containers, such as the closure apparatus which can move and handle the containers at enormous speed and can consequently also shake them so that, for example carbon dioxide escapes from the filling material in the container or oxygen is absorbed by the filling material in the container, consequently cannot falsify the measurement result. If, for example, the measurement takes place only after the closure apparatus, the influence of the closure apparatus would significantly influence the concentration of the gas in the filling material of the container so that ultimately hardly any reliable statement relating to the quality of the filling by the filling apparatus could be made. Causes for problems during filling can consequently be more quickly identified and overcome using the method according to the present disclosure. As a result of the selective analysis of the filling apparatus, for example, assembly operations lasting months in order to optimise the filling apparatus can be saved if, for example, the closure apparatus is actually responsible for an excessively high concentration of oxygen or an excessively low concentration of carbon dioxide in the filling material in the containers. Consequently, the potential for a discussion relating to the quality of the filling apparatus between the manufacturer and client of the filling apparatus can also be reduced.

In one embodiment, the gas is carbon dioxide or oxygen.

Preferably, the expression "concentration of a gas in the filling material" may relate to an indication which indicates a mass (for example, in g) or a volume (for example, in l or cm3) of the gas per mass (for example, in g) or volume (for example, in l) of the liquid or pasty filling material. In the context of the present disclosure, this term is also intended to be understood to refer to a gas content of the gas in the filling material.

In another embodiment, the filled container is manually removed in order to establish the concentration upstream of the closure apparatus (for example, without shaking the filled container).

In another embodiment, the method involves covering, preferably manually covering, the filled container with a lid, preferably in a substantially gas-tight manner, prior to measuring the concentration of the gas. As a result of the lid, the container can be safely transported to the measuring device, even if the container has not yet even been closed as a result of the removal of the container upstream of the closure apparatus. A change of the atmosphere in the upper space of the filled container can also be prevented, which has an influence on the gas exchange between the upper space and filling material in the container.

In another embodiment, the filled container is covered with the lid in the stationary state without the concentration of the gas in the filling material being significantly changed and/or without shaking the filled container. Advantageously, additional disruptive factors or sources of concern which can influence the gas concentration in the container can consequently be excluded.

In one embodiment, the filled container is covered with the lid directly downstream of the filling apparatus and/or upstream of the closure apparatus. Consequently, the container can advantageously be covered with the lid where applicable before or directly during the removal.

In another embodiment, the lid is identical to those lids with which the closure apparatus closes the containers, preferably bottles. Alternatively, the lid may, for example, be an adapter lid which preferably differs from those lids with which the closure apparatus closes the containers, preferably cans. Advantageously, the technique can consequently be used both with bottles, for example, PET bottles or glass bottles, which use, for example, a screw closure, and with cans with a corresponding adapter lid.

In another embodiment, the adapter lid has a, preferably penetrable, opening through which the filling material is conveyed to the measuring device and/or to which the measuring device is or can be connected.

In one variant, the adapter lid has a seal, preferably an O-ring, for sealing with respect to the filled container (for example, with respect to an outer cover or inner cover of the container), preferably on a circumferential collar portion of the adapter lid.

In another variant, the measurement of the concentration of the gas involves perforating the lid with a perforation apparatus and/or introducing a line portion, to which the measuring device is or can be connected, into the filling material in the filled container.

It is possible for the line portion to be a portion of the perforation apparatus, for example, the portion by means of which the lid is perforated (for example, in the region of the opening of the lid).

In another variant, the measurement of the concentration of the gas involves pressing out and/or drawing out the filling material from the filled container in the direction towards the measuring device.

In one embodiment, a conveying gas, preferably carbon dioxide or nitrogen, is introduced into the filled container, preferably into an upper space of the filled container, so that the filling material is pressed out of the filled container in the direction towards the measuring device. Advantageously, it is made possible to convey the filling material to the measuring device in a simple manner without the filling material becoming contaminated by oxygen in the conveying gas.

In one embodiment, a purge gas, for example, carbon dioxide or nitrogen, is introduced into a line between the filled container and the measuring device in order to purge the line before the filling material is directed through the line to the measuring device. Advantageously, therefore, it is possible to prevent the filling material from becoming contaminated by oxygen in the line on the way to the measuring device, whereby the measurement result could be falsified.

In another embodiment, the method further involves adapting an operation and/or a configuration (for example, construction, assembly and/or control) of the filling apparatus depending on the measured concentration. Advantageously, therefore, based on the measured concentration, which has not been influenced by disruptive factors located downstream of the filling apparatus, it is possible to identify in a very selective manner whether the operation or the configuration of the filling apparatus should be adapted (for example, optimised) in order to obtain the desired concentration of the gas in the filling material in the container directly downstream of the filling apparatus in an operationally reliable manner.

In another embodiment, the method further involves measuring another concentration of the gas in the filling material before the filling material is poured into the container and/or in a filling material supply line to the filling apparatus, wherein the filling material in order to measure the additional concentration of the gas is preferably drawn from a delivery valve of the filling material supply line. Optionally, the method may further involve establishing a concentration change of the gas via the filling apparatus depending on the measured concentration and the measured additional concentration. Advantageously, therefore, a change of the concentration of the gas which is actually brought about by the handling in the filling apparatus can be derived in order where applicable to identify potential for optimisation in the filling apparatus or to identify that the filling apparatus has already been adjusted as desired or in an optimum manner.

In another embodiment, the adaptation of the operation and/or the configuration (for example, construction, assembly and/or control) of the filling apparatus is further carried out in accordance with the measured additional concentration. Preferably, the adaptation can be carried out (for example, only) under the condition that the concentration change of the gas via the filling apparatus is greater than or less than a predetermined limit value.

Preferably, a container treatment installation may be configured to produce, clean, coat, check, fill, close, label, print and/or package containers for liquid media, preferably drinks or liquid foods.

For example, the containers may be in the form of bottles, cans, canisters, cartons, flasks, etcetera.

The above-described preferred embodiments and features of the invention can be freely combined with each other.

BRIEF DESCRIPTION OF THE FIGURES

Further details and advantages of the invention are described below with reference to the appended drawings, in which.

DETAILED DESCRIPTION OF EXEMPLARY EMBODIMENTS

Figure 1:
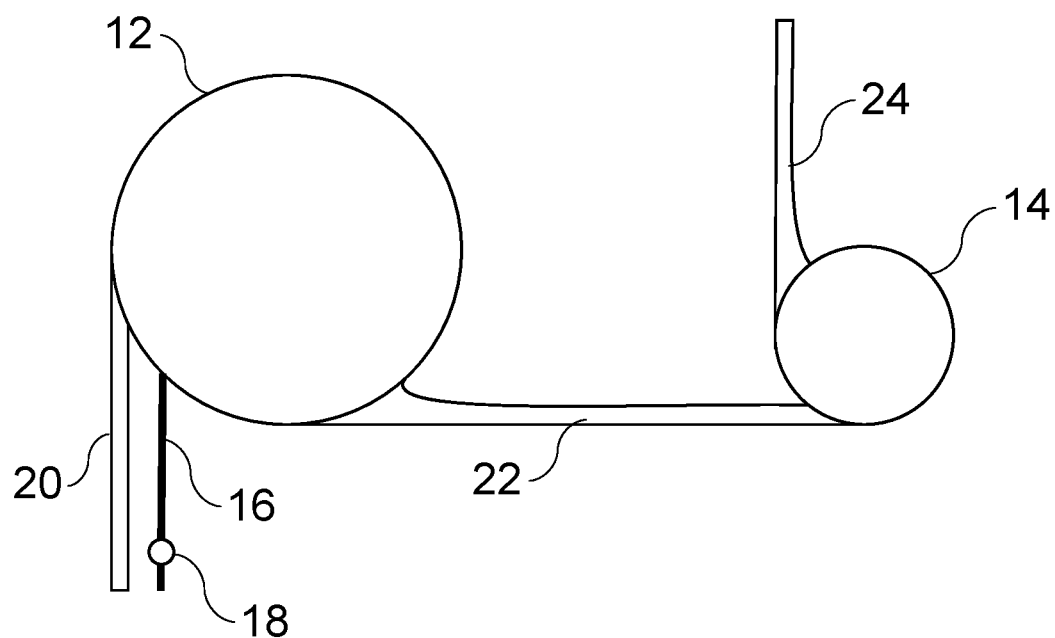
FIG. 1 shows a schematic view of a container treatment installation.

FIG. 1 shows a container treatment installation 10. The container treatment installation 10 has a filling apparatus 12 for filling containers and a closure apparatus 14 for closing containers. The closure apparatus 14 is arranged downstream of the filling apparatus 12 (with respect to the containers).

In a particularly preferred manner, the container treatment installation is constructed for handling cans, such as drinks cans (for example, 0.33 l or 0.5 l cans). Accordingly, the filling apparatus 12 is preferably configured for filling cans and the closure apparatus 14 is preferably configured for closing cans.

However, it is in principle also possible to apply the techniques of the present disclosure to container treatment installations which can handle a different type of container.

Such containers may, for example, be in the form of bottles, canisters, cartons, flasks, etcetera.

The filling apparatus 12 is preferably in the form of a filling carousel. The closure apparatus 14 is preferably in the form of a closure carousel. However, other construction types for the filling apparatus 12 and/or the closure apparatus 14 are also conceivable, for example, an embodiment as a linear filler or as a linear closure member.

The filling apparatus 12 can fill the containers with a filling material, for example, a drink or a food. The filling material is preferably a liquid or pasty medium. In a particularly preferred manner, the filling material is oxygen-sensitive, such as, for example, beer.

The filling apparatus 12 may have a plurality of filling valves for simultaneously filling a plurality of containers. For example, the filling valves may be arranged around a circumference of the filling apparatus 12 which is in the form of a filling carousel.

The filling apparatus 12 may have a product or filling material supply line 16. Via the filling material supply line 16, the filling material can be supplied to the filling apparatus 12 (and consequently to the filling valves of the filling apparatus 12). It is possible for the filling material supply line 16 to have, for example, a delivery valve 18, for example, a product tap. At the delivery valve 18, the filling material can be drawn, for example, for checks, for example, manually or automatically.

The filling apparatus 12 may have a container supply line 20. Via the container supply line 20, containers can be supplied to the filling apparatus 12 for filling. The container supply line 20 may, for example, have one or more container conveyors. The container conveyor(s) may, for example, have at least one transport star-like member (for example, filling apparatus inlet star-like member) and/or linear conveyor.

A transport apparatus 22 of the container treatment installation 10 may be arranged downstream of the filling apparatus 12. The transport apparatus 22 can connect the filling apparatus 12 and the closure apparatus 14 to each other. The transport apparatus 22 can be configured to transport containers from the filling apparatus 12 to the closure apparatus 14. The transport apparatus 22 may have one or more container conveyors. The container conveyor(s) may, for example, have at least one transport star-like member (for example, filling apparatus outlet star-like member and/or closure apparatus inlet star-like member) and/or linear conveyor.

The closure apparatus 14 may close the containers. Preferably, the closure apparatus 14 can close the containers which are in the form of cans with a can lid. The can lid can be securely connected to the container, for example, by means of mechanical shaping of the can lid and/or the container. The can lid itself may in turn have a closure which can be opened, as known, for example, with drinks cans.

However, it is also possible for the closure apparatus 14 to be configured to close another type of container, that is to say, not cans. Accordingly, the closure apparatus 14 may close the containers, for example, with a lid, a cork, a crown cap or a screw closure. The closure apparatus 14 may have a plurality of closure stations for simultaneously closing a plurality of containers. For example, the closure stations may be arranged around a circumference of the closure apparatus 14 which is in the form of a closure carousel.

The containers which are closed by the closure apparatus 14 can leave the closure apparatus 14 via a container outlet 24. The container outlet 24 may transport the closed containers, for example, to at least one additional handling apparatus of the container treatment installation. The container outlet 24 may have one or more container conveyors. The container conveyor(s) may, for example, have at least one transport star-like member (for example, filling apparatus outlet star-like member and/or closure apparatus inlet star-like member) and/or linear conveyor.

It is possible for the container treatment installation 10 in addition to the filling apparatus 12 and the closure apparatus 14 to have additional handling apparatuses for handing containers (not illustrated). For example, the container treatment installation 10 may additionally have a handling apparatus for producing, checking, coating, cleaning labelling, printing and/or packing containers.

Figure 2:
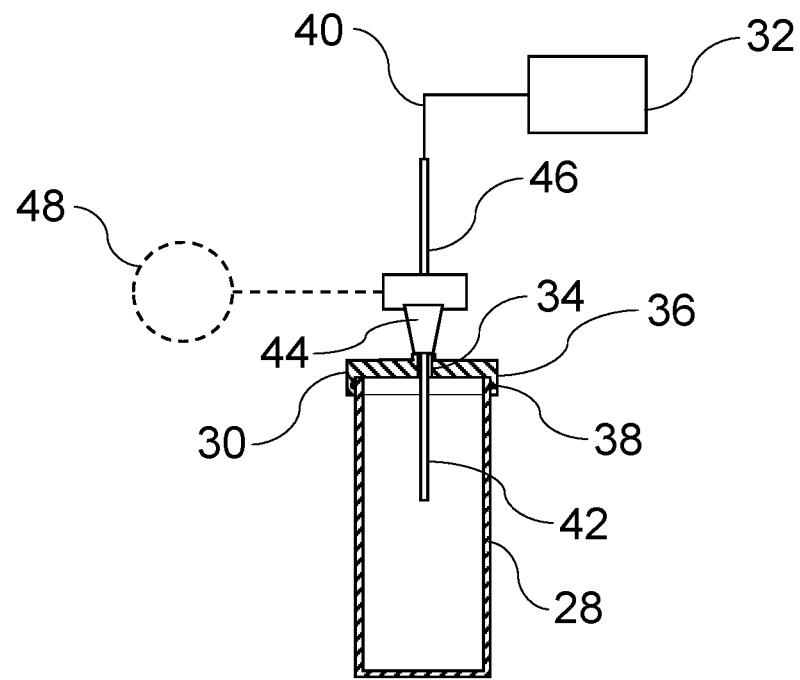
FIG. 2 shows a schematic structure for measuring a concentration of a gas in a filling material of a container, wherein the container and an adapter lid are illustrated in section.

FIG. 2 shows an exemplary measurement structure 26 for measuring a concentration of a gas in the filling medium of a container 28.

The measurement structure 26 has the container 28, an adapter lid 30 and a measuring device 32. The container 28 is preferably in the form of an incomplete can in which the conventional can closure is missing, as illustrated.

The adapter lid 30 is preferably constructed to close the container 28 which is in the form of an incomplete can and in which the conventional can closure/lid is missing. In place of a conventional closure/lid, the container 28 can consequently be closed by means of the adapter lid 30.

Preferably, the adapter lid 30 has an opening 34. For example, the opening 34 may be arranged centrally in the adapter lid 30. The opening 34 may preferably connect an upper side of the adapter lid 30 to a lower side of the adapter lid 30. The opening 34 may be in the form of a through-hole through the adapter lid 30.

It is possible for the opening 34 to be a part or a portion of a securing connection for the preferably gas-tight, releasable connection of the measuring device 32. The securing connection may, for example, have a securing portion, such as, for example, a thread, a bayonet closure, a plug element, a plug element receiving member, a locking element or a locking element receiving member for connecting the measuring device 32.

The adapter lid 30 may preferably be configured in a disc-like manner and may have a circumferential collar portion or flange 36. In order to close the container 28, the collar portion 36 may completely circumferentially engage around or surround an outer cover of the container 28. A seal 38, such as, for example, an O-ring may further be arranged on the collar portion 36. The seal 38 may seal between the adapter lid 30 or the collar portion 36 thereof and the container 28 or the outer cover thereof in a gas-tight manner.

A connection between the adapter lid 30 and the container 28 may be releasable. Preferably, the adapter lid 30 may be pushed or placed onto the unclosed container 28.

The measuring device 32 may be releasably connected to the adapter lid 30 (or another lid) in order to measure a concentration of a gas, preferably carbon dioxide ($CO_2$) or oxygen. The measuring device 32 may be connected to the adapter lid 30 and consequently to the container 28 by means of a line 40.

The measuring device 32 may use any known technique in order to measure a concentration of the gas. The measuring device 32 may additionally output the measured concentration, for example, via an indicator unit or in the form of a corresponding electrical (for example, analogue or digital) signal which indicates the measured concentration.

The measuring device 32 may be connected to the adapter lid 30 (or another lid), preferably to the opening 34 thereof, by means of a seal 44. For example, the seal 44 may be in the form of a truncated wedge or truncated cone for inserting into the opening 34.

Preferably, a line portion 42 which is connected to the measuring device 32 protrudes through the opening 34 directly into the filling medium in the container 28. Via this line portion 42, at least a portion of the filling medium in the container 28 can be directed to the measuring device 32. In this portion of the filling medium from the container 28, the measuring device 32 can measure the concentration of the gas.

It is possible for the measurement structure 26 to further have a perforation apparatus 46 and/or a gas source 48.

The perforation apparatus 46 may be constructed to perforate the adapter lid 30 (or another lid) in the region of the where applicable closed opening 34 or to be guided through the opening 34 in order to be introduced with the line portion 42 in the filling medium in the container 28.

The gas source 48 may be connected to a line system which connects the measuring device 32 and the opening 34 of the adapter lid 30 to each other. The gas source 48 may, for example, provide nitrogen or carbon dioxide. By means of the gas source 48, gas can be directed into the line system. The gas may, for example, be used as purge gas in order to purge the line system. Alternatively or additionally, the gas can be used as conveying gas for pressing out the filling medium in the container 28 through the line portion 42 in the direction towards the measuring device 32. To this end, the gas may, for example, be supplied to an upper space of the container 28.

Even if the particularly preferred embodiment is described herein with the container 28 which is in the form of a can and the adapter lid 30, it should be noted that in embodiments in which the containers 28 are, for example, not cans (for example, glass or PET bottles), in place of the adapter lid 30 another lid can be used to close the container 28 for connecting the measuring device 32. The lid may preferably be of the same type as the one used by the closure apparatus 14 to close the containers 28, for example, a screw closure.

A method for monitoring a container treatment installation is described below. The method is described by way of example with reference to FIGS. 1 to 3.

The method involves filling a container 28 with a filling material by means of the filling apparatus 12. For example, the container may be filled with the filling medium by the filling apparatus 12 as one of several containers 28. During filling, the container 28 may be positioned below a filling valve of the filling apparatus 12. During filling, the container 28 may be pressed onto the filling valve, or there may be a gap between the container 28 and the filling valve. The filling apparatus 12 may receive the filling medium via the filling material supply line 16. The filling apparatus 12 may receive the container 28 which is intended to be filled via the container supply line 20.

It is possible for the container 28, prior to being filled with the filling medium, to be evacuated at least once, purged at least once with a production gas (for example, inert gas, such as carbon dioxide) and/or pretensioned with a production gas (for example, inert gas, such as carbon dioxide). The evacuation, purging and/or pretensioning can be carried out by means of the filling apparatus 12.

The method further involves measuring a concentration of a gas in the filling medium of the filled container 28 by means of the measuring device 32. To this end, the filling material can be directed out of the container 28 to the measuring device 32.

The container 28 which is filled with the filling medium by means of the filling apparatus 12 is removed in order to measure the concentration upstream of the closure apparatus 14, for example, directly downstream of the filling apparatus 10 and/or a position on the transport apparatus 22. During removal, the transport apparatus 22 for transporting containers 28 may be moving or stationary.

Alternatively, the concentration of the gas in the filling medium of the filled container 28 is measured upstream of the closure apparatus 14 without the filled container 28 being removed from a position on the transport apparatus 22 to this end. In this instance, the concentration of the gas in the filling medium may be measured, for example, directly at the transport apparatus 22.

The removal of the filled container 28 can preferably be carried out manually/by hand. However, it is also possible for the filled container 28 to be directed, for example, automatically out of a container flow and consequently removed.

The method may further involve covering, preferably manually covering, the filled container 28 with a (for example, adapter) lid 30 prior to measuring the concentration of the gas. The lid 30 may preferably cover the container 28 in a gas-tight manner. The lid 30 may, for example, be configured in the same manner as the adapter lid 30 (see FIG. 2), particularly when the container 28 is a can.

The covering with the lid 30 is preferably carried out when the container 28 is stationary, for example, when the container 28 is retained or supported by the transport apparatus 22 and the transport apparatus 22 is stationary. Preferably, the filled container 28 can be covered with the lid 30 directly downstream of the filling apparatus 12.

However, the container may, for example, also be removed from the transport apparatus 22, placed elsewhere and then covered with the lid 30. Alternatively, the lid 30 may also be covered with the lid 30 during a movement of the container 28, wherein there is preferably brought about no shaking of the container 28 and consequently no significant change of the concentration of the gas in the filling material in the container 28.

The measurement or establishment of the concentration of the gas by means of the measuring device 32 may involve connecting the measuring device 32 to the lid 30, for example, the opening 34 of the lid 30. In this instance, for example, the perforation apparatus 46 can be used in order to perforate the lid 30. The line portion 42 may be introduced in the filling material in the container 28 and direct the filling material to the measuring device 32.

It is possible for the filling material to be drawn from the container 28 to the measuring device 32, for example, with a pump (not illustrated). Alternatively or additionally, the filling material can be pressed out of the container 28 by supplying a (for example, conveying) gas into the upper space of the container 28 from the container 28 via the line portion 42 in the direction towards the measuring device 32. The gas can be directed from the gas source 48 to the container 28. It is also possible for the gas from the gas source 48 to purge the line between the container 28 and the measuring device 32.

The method may further involve adapting an operation and/or a configuration of the filling apparatus 12 in accordance with the measured concentration.

For example, an oxygen concentration which is above a predetermined limit value can be measured. The operation and/or the configuration of the filling apparatus 12 can be adapted in order to reduce the oxygen concentration in the filling material in containers 28 which are subsequently filled.

On the other hand, for example, it is possible to measure a carbon dioxide concentration which is below a predetermined limit value. The operation and/or the configuration of the filling apparatus 12 can be adapted in order to increase the carbon dioxide concentration in the filling material in containers 28 which are subsequently filled.

The method may further involve measuring an (additional) concentration of the gas in the filling material and the adaptation of the operation and/or the configuration of the filling apparatus 12 may further be dependent on the measured additional concentration.

This (additional) concentration of the gas can be measured in the filling material before the filling material is poured from the filling apparatus 12 into the containers 28. For example, filling material can be drawn at the delivery valve 18 in the filling material supply line 16 and examined for the (additional) concentration, for example, using the measuring device 32.

From the measured concentration of the filling material in the container 28 and the measured (additional) concentration of the filling material prior to filling, a concentration change of the gas in the filling material can be derived or established by means of the filling apparatus 12. The concentration may have increased, decreased or remained substantially the same.

If, for example, an increase of the oxygen concentration which exceeds a predetermined limit value has been established via the filling apparatus 12, the operation and/or the configuration of the filling apparatus 12 can be adapted in order to obtain a low oxygen concentration in the filling material in the containers 28 in containers 28 which are subsequently filled.

If, for example, a decrease of the carbon dioxide concentration which exceeds a predetermined limit value has been established via the filling apparatus 12, the operation and/or the configuration of the filling apparatus 12 can be adapted in order to obtain a higher carbon dioxide concentration in the filling material in the containers 28 in containers 28 which are subsequently filled.

The method consequently enables a very precise examination of the extent to which the filling apparatus 12 is responsible for an increase or decrease of the gas in order to be able to react in a correspondingly selective manner. Therefore, the method is advantageous over other methods, as described below with reference to FIG. 3.

Figure 3:
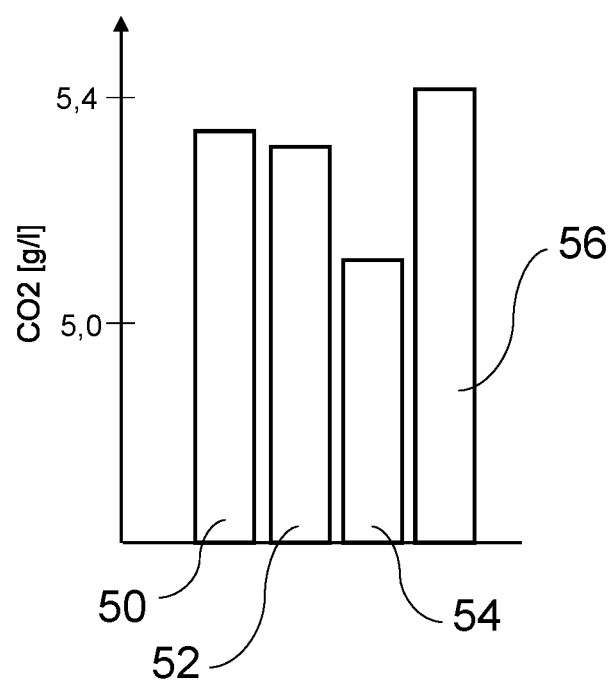
FIG. 3 shows a bar chart for indicating concentrations of carbon dioxide in the filling medium as measured by way of example at different positions of a container treatment installation.

FIG. 3 shows a bar chart having four bars 50, 52, 54, 56, which indicate the actually measured carbon dioxide concentrations in a container treatment installation for containers 28 which are in the form of cans.

The bar 50 indicates a carbon dioxide concentration in the filling material which has been measured at the delivery valve 18. The bar 52 indicates a carbon dioxide concentration in the filling material of filled, closed containers 28 which was measured downstream of the closure apparatus 14. The bar 54 indicates a carbon dioxide concentration in the filling material of filled containers 28 which was measured after the filled container 28 was powerfully agitated. As a result of the agitation, the carbon dioxide concentration in the filling material in the filled container 28 is substantially reduced. The bar 56 indicates a carbon dioxide concentration in the filling material of filled containers 28 which was measured according to the present monitoring method upstream of the closure apparatus 14, for example, after corresponding removal of the container 28.

When bars 50 and 52 are compared, a decrease of the carbon dioxide concentration is apparent. When the bars 50 and 56 are compared, in contrast, an increase of the carbon dioxide concentration is evident. The can which has been removed after the closure apparatus 14 for measurement has approximately 0.1 g/l $CO_2$ less in the filling material than the can which has been removed between the filling apparatus 12 and the closure apparatus 14 for measurement (see bars 52 vs. 56).

That is to say, only the comparison of the bars 50 and 56 can provide reliable information relating to how the concentration of carbon dioxide via the filling apparatus 12 has changed or what carbon dioxide content there is in the filling material in the container 28 directly after filling. If only the bars 50 and 52 were taken into consideration, there would potentially be incorrect estimates or incorrect diagnoses. It would not be taken into account that, as a result of the movements and disturbances of the containers 28 in the closure apparatus 14, the containers 28 are shaken and consequently a carbon dioxide concentration in the filling material in the containers 28 can decrease. The quality of the (low-oxygen) filling of the filling apparatus 12 would consequently be underestimated. Only by taking into account the column 56 can a conclusion be selectively drawn relating to the actual absorption or discharge of $CO_2$ during the filling. This, as explained, can be measured in the cans by means of the measurement structure 26 which is described with reference to FIG. 2 using the adapter lid 30 for the container which is in the form of a can before the container 28 has been closed by the closure apparatus 14.

FIG. 3 relates by way of example to the measurement of carbon dioxide concentrations. However, the technique can, for example, also be used for the measurement of oxygen concentrations.

The invention is not limited to the preferred embodiments described above. Instead, a large number of variants and modifications which also make use of the notion of the invention and are therefore included within the protective scope are possible. In particular, the invention also claims protection for the subject-matter and the features of the dependent claims regardless of the claims referred to. In particular, the individual features of the independent claim 1 are in each case disclosed independently of each other. In addition, the features of the subordinate claims are disclosed independently of all the features of the independent claim 1 and are, for example, disclosed independently of the features of the independent claim 1.

LIST OF REFERENCE NUMERALS

10 Container treatment installation
12 Filling apparatus
14 Closure apparatus
16 Filling material supply line
18 Delivery valve
20 Container supply line
22 Transport apparatus
24 Container outlet
26 Measurement structure
28 Container
30 Adapter lid
32 Measuring device
34 Opening
36 Collar portion
38 Seal
40 Line
42 Line portion 44 Seal
46 Perforation apparatus
48 Gas source
50-56 Bars to indicate the carbon dioxide concentration

The invention claimed is:

1. A method for monitoring a container treatment installation which has a filling apparatus for filling containers and a closure apparatus for closing containers, wherein the closure apparatus is arranged downstream of the filling apparatus, the method comprising:
    filling a container with a filling material using the filling apparatus;
    measuring a concentration of a gas in the filling material of the filled container using a measuring device, wherein the filled container is removed in order to measure the concentration upstream of the closure apparatus or the concentration is measured upstream of the closure apparatus.

2. The method according to claim 1, wherein:
    the gas is carbon dioxide or oxygen.

3. The method according to claim 1, wherein:
    the filled container is manually removed in order to establish the concentration upstream of the closure apparatus.

4. The method according to claim 1, further comprising:
    covering the filled container with a lid prior to measuring the concentration of the gas.

5. The method according to claim 4, wherein at least one of:
    the filled container is covered with the lid in a stationary state without the concentration of the gas in the filling material being significantly changed;
    the filled container is covered with the lid in a stationary state without shaking the filled container; and
    the filled container is covered with the lid in a substantially gas-tight manner.

6. The method according to claim 5, wherein at least one of:
    the measurement of the concentration of the gas involves perforating the lid with a perforation apparatus; and
    the measurement of the concentration of the gas involves introducing a line portion, to which the measuring device is connected or connectable, into the filling material in the filled container.

7. The method according to claim 4, wherein at least one of:
    the filled container is covered with the lid directly downstream of the filling apparatus; and
    the filled container is covered with the lid upstream of the closure apparatus.

8. The method according to claim 4, wherein:
    the lid is identical to those lids with which the closure apparatus closes the containers, or
    the lid is an adapter lid which differs from those lids with which the closure apparatus closes the containers.

9. The method according to claim 8, wherein:
    the adapter lid has an opening through which the filling material is conveyed to the measuring device or to which the measuring device is connectable.

10. The method according to claim 9, wherein:
    the opening is penetrable.

11. The method according to claim 8, wherein:
    the adapter lid has a seal for sealing with respect to the filled container.

12. The method according to claim 11, wherein at least one of:
    the seal is an O-ring; and
    the adapter lid has the seal on a circumferential collar portion of the adapter lid.

13. The method according to claim 1, wherein at least one of:
    the measurement of the concentration of the gas involves pressing out the filling material from the filled container in the direction towards the measuring device; and
    the measurement of the concentration of the gas involves drawing the filling material from the filled container in the direction towards the measuring device.

14. The method according to claim 1, wherein at least one of:
    a conveying gas is introduced into the filled container so that the filling material is pressed out of the filled container in a direction towards the measuring device; and
    a purge gas is introduced into a line between the filled container and the measuring device in order to purge the line before the filling material is directed through the line to the measuring device.

15. The method according to claim 1, further comprising at least one of:
    adapting an operation of the filling apparatus depending on the measured concentration; and
    adapting a configuration of the filling apparatus depending on the measured concentration.

16. The method according to claim 1, further comprising at least one of:
    measuring an additional concentration of the gas in the filling material before the filling material is poured into the container, and
    measuring an additional concentration of the gas in the filling material in a filling material supply line to the filling apparatus.

17. The method according to claim 16, wherein:
    the filling material in order to measure the additional concentration of the gas is drawn from a delivery valve of the filling material supply line.

18. The method according to claim 16, further comprising:
    establishing a concentration change of the gas via the filling apparatus depending on the measured concentration and the measured additional concentration.

19. The method according to claim 16, wherein at least one of:
    the adaptation of the operation of the filling apparatus is further carried out in accordance with the measured additional concentration, and
    the adaptation of the configuration of the filling apparatus is further carried out in accordance with the measured additional concentration.

20. The method of claim 19, wherein:
    the adaptation is carried out under the condition that the concentration change of the gas via the filling apparatus is greater than or less than a predetermined limit value.

* * * * *